US010973655B2

(12) United States Patent
Abu-Mulaweh et al.

(10) Patent No.: US 10,973,655 B2
(45) Date of Patent: Apr. 13, 2021

(54) CORPECTOMY CAGE

(71) Applicant: Nexxt Spine, LLC, Noblesville, IN (US)

(72) Inventors: Alaedeen Abu-Mulaweh, Noblesville, IN (US); Austin Clemens, Indianapolis, IN (US); Andrew Elsbury, McCordsville, IN (US)

(73) Assignee: NEXXT SPINE, LLC, Noblesville, IN (US)

( * ) Notice: Subject to any disclaimer, the term of this patent is extended or adjusted under 35 U.S.C. 154(b) by 160 days.

(21) Appl. No.: 16/514,264

(22) Filed: Jul. 17, 2019

(65) Prior Publication Data

US 2020/0237523 A1  Jul. 30, 2020

Related U.S. Application Data

(60) Provisional application No. 62/797,586, filed on Jan. 28, 2019.

(51) Int. Cl.
*A61F 2/44* (2006.01)
*A61F 2/30* (2006.01)

(52) U.S. Cl.
CPC .... *A61F 2/447* (2013.01); *A61F 2002/30593* (2013.01); *A61F 2002/30841* (2013.01)

(58) Field of Classification Search
CPC ...... A61F 2/30744; A61F 2/44; A61F 2/4455; A61F 2/447; A61F 2002/30151; A61F 2002/30593; A61F 2002/30616; A61F 2002/30841
See application file for complete search history.

(56) References Cited

U.S. PATENT DOCUMENTS

| | | | | |
|---|---|---|---|---|
| 6,086,613 A * | 7/2000 | Camino | ............ | A61F 2/30744 623/17.16 |
| 8,545,567 B1 * | 10/2013 | Krueger | ............ | A61F 2/4684 623/17.16 |
| 9,700,425 B1 * | 7/2017 | Smith | ............ | A61F 2/4611 |
| 10,278,833 B2 * | 5/2019 | Howard | ............ | A61F 2/446 |
| 10,278,834 B2 * | 5/2019 | Howard | ............ | A61F 2/4611 |
| 10,881,528 B2 * | 1/2021 | Howard | ............ | A61F 2/4465 |
| 2009/0036985 A1 * | 2/2009 | Whiting | ............ | A61F 2/30744 623/17.11 |
| 2009/0112325 A1 * | 4/2009 | Refai | ............ | A61F 2/30734 623/17.16 |
| 2017/0252182 A1 * | 9/2017 | Acosta | ............ | A61F 2/44 |

(Continued)

*Primary Examiner* — Eric S Gibson
(74) *Attorney, Agent, or Firm* — Maginot, Moore & Beck, LLP

(57) ABSTRACT

A corpectomy cage includes a main body, a first end cap, and a second end cap. The main body is shaped as a hollow rectangular prism, and includes a first end and a second end. The first end has a plurality of first receivers formed therein, and the second end has a plurality of second receivers formed therein. The first end cap includes a plurality of first legs configured to be received within respective first receivers to removably engage the first end cap with the first end of the main body. Similarly, the second end cap includes a plurality of second legs configured to be received within respective second receivers to removably engage the second end cap with the second end of the main body. Each of the end caps further includes a plurality of teeth arranged opposite the plurality of legs.

18 Claims, 9 Drawing Sheets

(56) References Cited

U.S. PATENT DOCUMENTS

| | | | |
|---|---|---|---|
| 2018/0071107 A1* | 3/2018 | Howard | A61F 2/44 |
| 2018/0098861 A1* | 4/2018 | Howard | A61F 2/4611 |
| 2019/0224023 A1* | 7/2019 | Howard | A61F 2/44 |
| 2020/0237523 A1* | 7/2020 | Abu-Mulaweh | A61F 2/4455 |

* cited by examiner

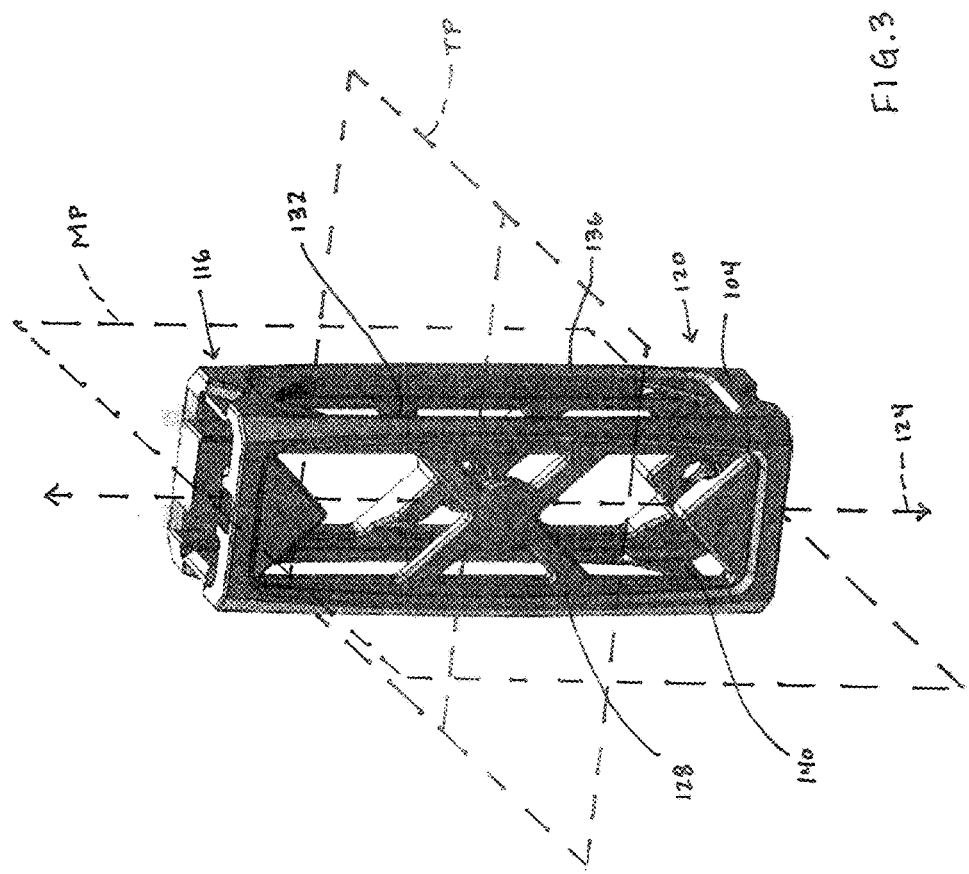

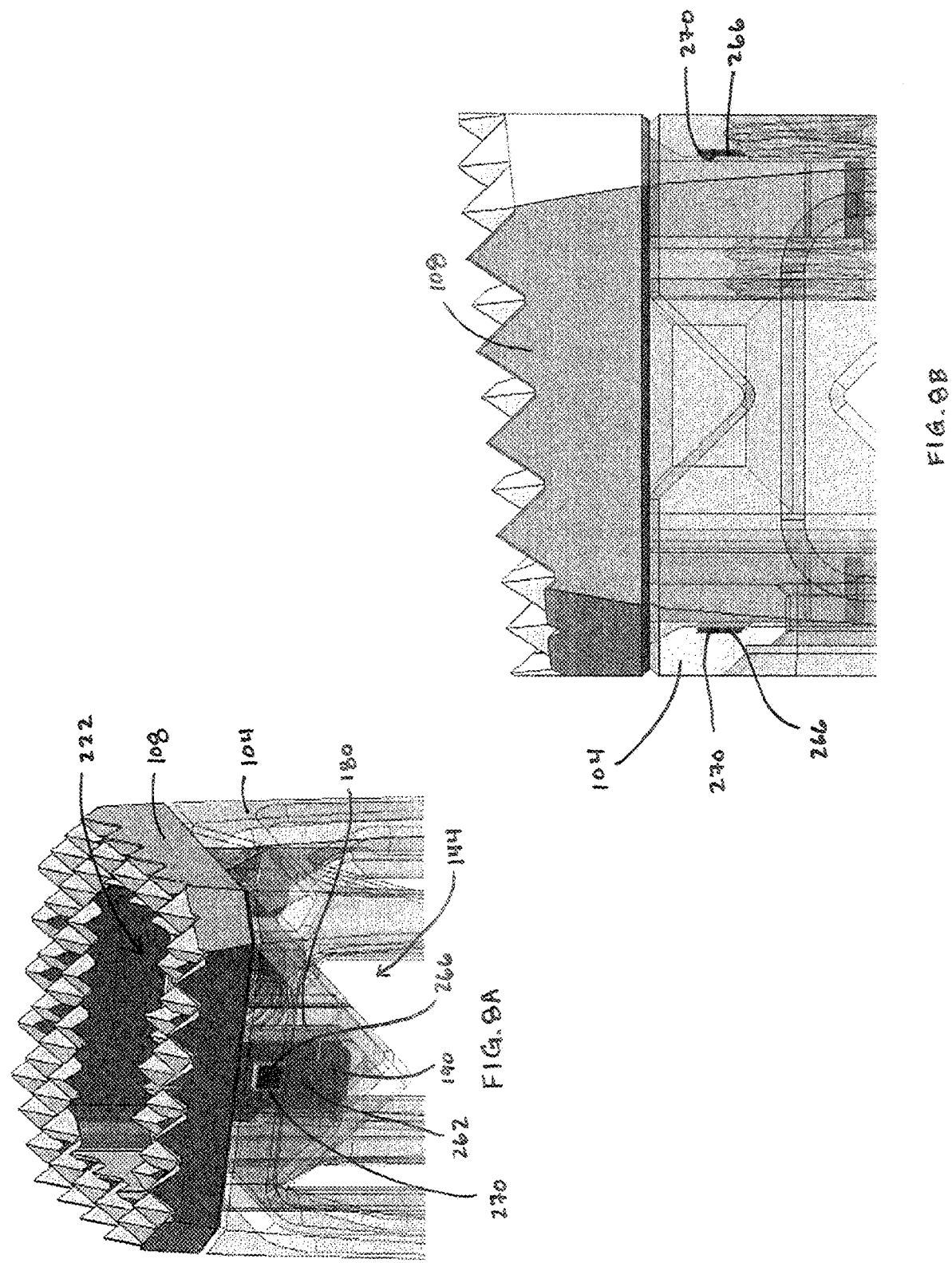

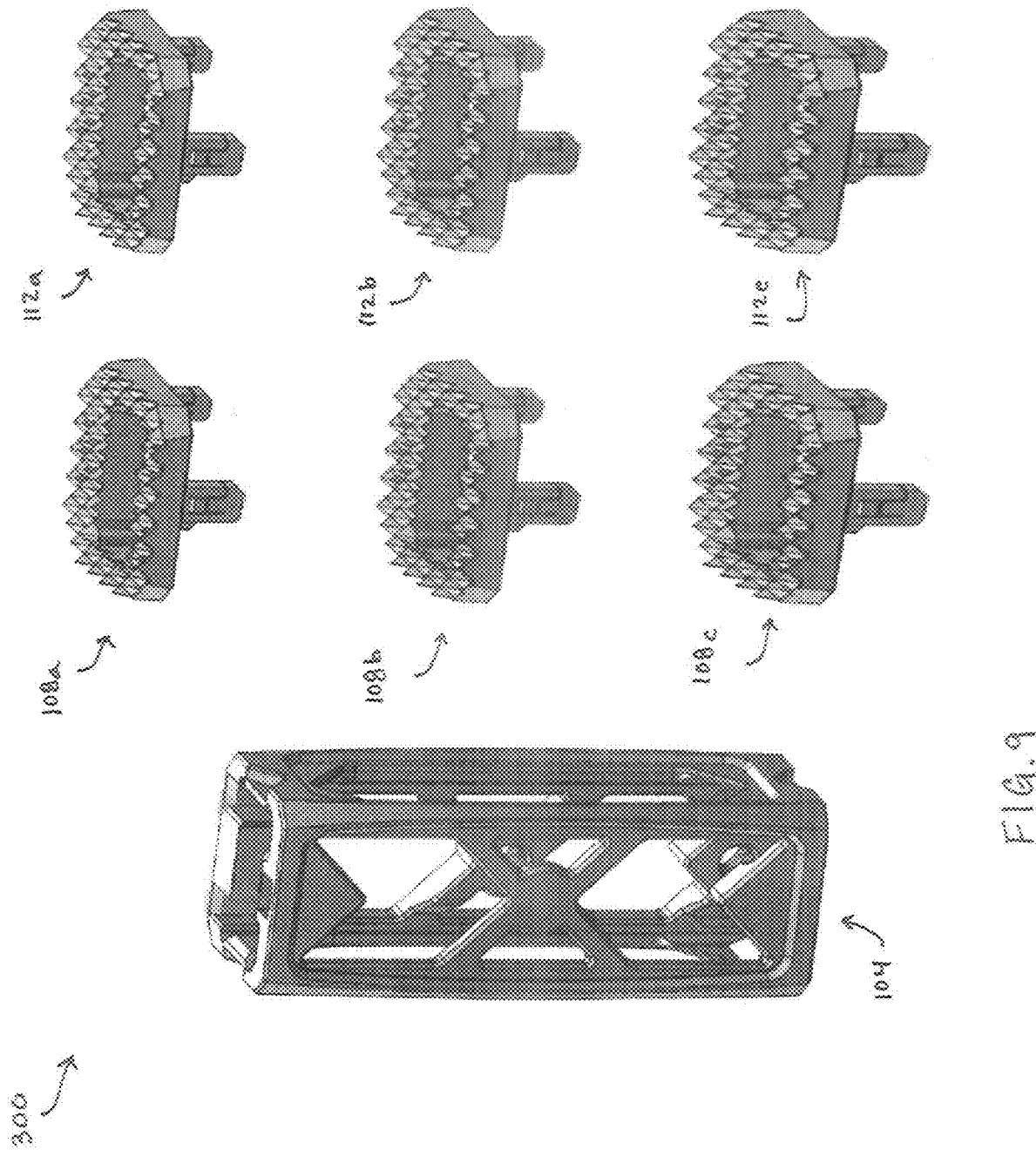

CORPECTOMY CAGE

PRIORITY CLAIM

This application claims priority to provisional application No. 62/797,586, filed on Jan. 28, 2019, entitled "Corpectomy Cage," and incorporates herein the disclosure of said application in its entirety.

BACKGROUND

The present disclosure relates to a corpectomy cage to be implanted in a patient. A corpectomy is a surgical procedure wherein all or a portion of the vertebral body and adjacent intervertebral discs are removed to relieve pressure or decompress the spinal cord and nerves. A corpectomy cage is a rigid body that is used to fill the space created by the vertebrae removal and maintain the desired post-operative spacing and angles between remaining vertebral bodies or discs.

To provide a cage having the height necessary to maintain the desired post-operative spacing, two types of cages are generally available, namely a fixed height cage and an expandable cage. A fixed height cage is manufactured to have a specific height selected to best fit the cavity and maintain the desired spacing. However, due to practical constraints, a fixed height cage is not specifically manufactured for each patient or surgery. Moreover, the exact required height specifications of the corpectomy cage may not be known until surgery is underway. Accordingly, fixed height cages are provided in premade sets with multiple cages having different heights. The surgeon then selects one fixed height cage from the set that best fits the cavity created by the removed vertebral body.

Alternatively, an expandable cage includes a physical mechanism that enables varying the height of the cage to meet the required height specifications. Thus, only one expandable cage is provided and is adjusted to best suit the cavity and desired spacing. Such expandable cages typically include telescoping members that can be adjusted by the physical mechanism and then fixed or set at the selected height prior to or after insertion.

Both types of cages have limitations and problems. Fixed height cages, which can include solid cages, have superior structural integrity, but are difficult to place. The fixed cage must be exactly the right height to fit in the cavity created by the removed vertebral body and to maintain the desired spacing. Otherwise, if the height of the cage is too large, it can cause over-distraction to the vertebral bodies or damage the vertebral body above and below the cage. If the height of the cage is too small, it can move from its position and will not be able to maintain the desired spacing. Thus, as mentioned above, fixed height cages are provided in sets having several cages of various heights to accommodate different patient anatomies and surgical applications. This inherently results in wasted materials. Additionally, only a finite number of pre-selected heights are available in any given set.

Because expandable cages are able to be adjusted precisely to the desired size, they are easier to place and are more able to meet the exact required height specification. However, the inclusion of the physical mechanism used to expand the cage increases the complexity of manufacture, which increases costs. Additionally, the physical mechanism may fail in vivo post-operatively, which can lead to catastrophic results.

In addition to the height of the cage, which is selected to maintain a desired spacing between remaining vertebral bodies or discs, the lordotic angle of the cage is also selected to accommodate different patient anatomies and surgical applications. The lordotic angle refers to the natural curvature of the lumbar and cervical regions of the spine. When all or a portion of the vertebral body and adjacent intervertebral discs are removed from the lumbar or cervical region of the spine, the end faces of the corpectomy cage that is inserted into the site and abut the remaining vertebral bodies or discs must be angled to maintain the desired post-operative curvature.

One way to provide the desired lordotic angles to the ends of the corpectomy cage is by fixed angle attachments that are interchangeably attachable to a main body of the cage. Fixed angle attachments can be selected for and attached to each of the ends of the corpectomy cage. Like the fixed height cage, fixed angle attachments are structurally stable, but must be provided in a set of attachments having a variety of angles. Thus, the fixed angle attachments are inherently available having only a finite number of predetermined fixed angles. Additionally, if the attachments are insecurely attached to the corpectomy cage, unintended movement or detachment of the attachments from the corpectomy cage in vivo post-operatively could lead to catastrophic results.

Another way to provide the desired lordotic angles to the ends of the corpectomy cage is by an integral adjustable mechanism or mechanisms that enables varying and setting the lordotic angle of each end of the cage independently. Such cages often include ends which rotate relative to the remainder of the cage to adjust the angle of the end surface relative to the remainder of the cage. Thus, one cage is provided and each end is adjusted to achieve the desired lordotic angle. Such cages having adjustable ends are more complex and costly to produce, and if the adjustable mechanism fails in vivo post-operatively, the results could be catastrophic.

It is possible to combine either of a fixed height and an expandable cage with either of fixed angle attachment ends and adjustable ends to achieve the desired height and lordotic angles of the corpectomy cage.

There is a need for a corpectomy cage having a height and lordotic angles that can be easily tailored to the anatomy of the patient and the specific surgical application.

SUMMARY

A corpectomy cage to be implanted in a patient has been developed. The corpectomy cage includes a fixed height cage, referred to herein as a main body, and fixed angle attachment ends, referred to herein as end caps. In particular, the corpectomy cage includes a main body shaped as a hollow rectangular prism. The main body includes a first end having a plurality of first receivers formed therein. The main body further includes a second end arranged opposite the first end. The second end has a plurality of second receivers formed therein. The corpectomy cage also includes a first end cap, and the first end cap includes a plurality of first legs. Each first leg is configured to be received within a respective first receiver of the plurality of first receivers to removably engage the first end cap with the first end of the main body. The first end cap further includes a plurality of first teeth arranged opposite the plurality of first legs. The corpectomy cage also includes a second end cap, and the second end cap includes a plurality of second legs. Each second leg is configured to be received within a respective second receiver of the plurality of second receivers to removably engage the second end cap with the second end of the main body. The second end cap further includes a plurality of second teeth arranged opposite the plurality of second legs.

A kit for a corpectomy cage to be implanted into the body has also been developed. The kit includes at least one main body shaped as a hollow rectangular prism. The main body includes a first end having a plurality of first receivers formed therein, and a second end arranged opposite the first end and having a plurality of second receivers formed therein. The kit further includes a plurality of end caps to be interchangeably coupled to the first and second ends of the main body. Each end cap includes a plurality of legs, each configured to be received within one of a first receiver and a second receiver to removably engage the end cap with one of the first and second ends of the main body. Each end cap further includes a plurality of first teeth arranged opposite the plurality of legs

BRIEF DESCRIPTION OF THE DRAWINGS

FIG. 3 depicts a perspective view of the main body of the corpectomy cage of FIG. 1 including planes of symmetry of the main body.

FIG. 8A depicts a partial perspective view of a line drawing of the end cap shown in FIGS. 4A and 4B engaged with the main body of the corpectomy cage shown in FIG. 1.

FIG. 8B depicts a partial side elevational view of a line drawing of the end cap shown in FIGS. 4A and 4B engaged with the main body of the corpectomy cage as shown in FIG. 8A.

FIG. 9 depicts a schematic view of a kit for a corpectomy cage, including a main body and a plurality of end caps.

DETAILED DESCRIPTION

Figure 1:
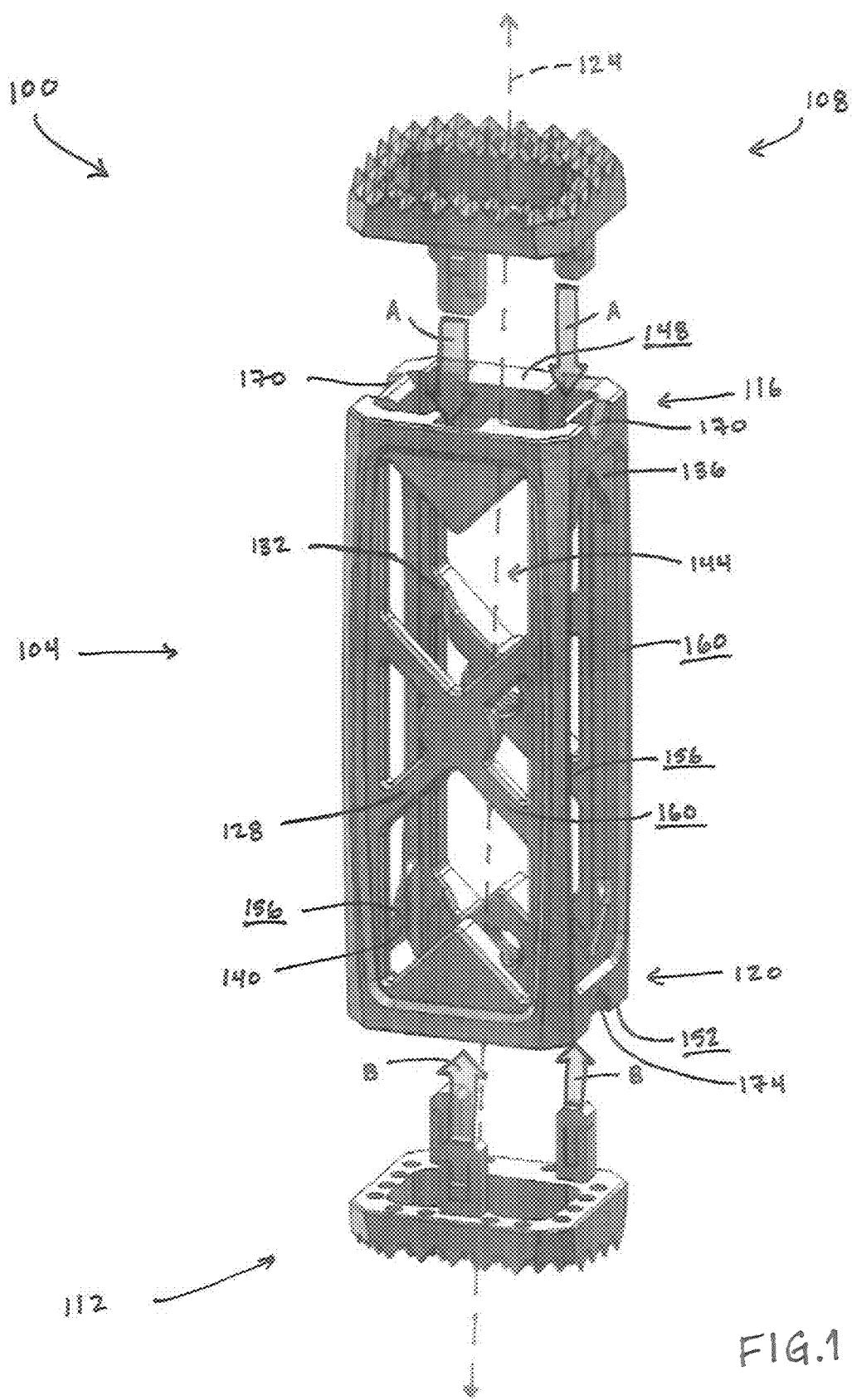
FIG. 1 depicts an exploded perspective view of the corpectomy cage, including a main body and two end caps.

FIG. 1 depicts an exploded view of a corpectomy cage 100, including a main body 104, a first end cap 108, and a second end cap 112. As described in further detail below, each of the first and second end caps 108, 112 is configured to be engaged with the main body 104 such that the corpectomy cage 100 is strong and sturdy once implanted within or between vertebrae in the body of a patient. More specifically, the first end cap 108 is configured to be removably engaged with a first end 116 of the main body 104 in the direction indicated by the arrows A, and the second end cap 112 is configured to be removably engaged with a second end 120 of the main body 104 in the direction indicated by the arrows B. As shown, the second end 120 is arranged opposite the first end 116. When the first end cap 108 and the second end cap 112 are engaged with the main body 104, the end caps 108, 112 and the main body 104 are coaxially aligned along a longitudinal axis 124 of the corpectomy cage 100. As used herein, the term "coaxially aligned" means that two separate bodies, each having its own axis of orientation, are aligned such that their axes are coincident with one another. In other words, their axes are defined by exactly the same points and appear to be a single axis.

The main body 104 is shaped as a hollow rectangular prism. The rectangular prismatic shape is beneficial as it allows the corpectomy cage 100 to be easily fitted into and accepted by the space within or between vertebrae that is formed by the removal of native tissue during the corpectomy, because the surgical tools and techniques typically used to perform a corpectomy naturally remove tissue in the form of a generally rectangular prismatic space. Additionally, the hollow shape is beneficial because it allows the corpectomy cage 100 to be filled with bone graft material to facilitate integration of the corpectomy cage 100 with surrounding native tissue once the corpectomy cage 100 has been implanted.

As a hollow rectangular prism, the main body 104 is made up of a front wall 128, a rear wall 132, a first side wall 136, and a second side wall 140. The front wall 128 and the rear wall 132 are arranged opposite one another, and the first side wall 136 and the second side wall 140 are arranged opposite one another. Each of the first side wall 136 and the second side wall 140 is also arranged to extend from the front wall 128 to the rear wall 132. Likewise, each of the front wall 128 and the rear wall 132 is arranged to extend from the first side wall 136 to the second side wall 140. Together, the front wall 128, rear wall 132, first side wall 136, and second side wall 140 delimit a longitudinal opening 144 within the interior of the main body. The longitudinal opening 144 extends along the longitudinal axis 124.

In the embodiment shown, the front wall 128 and the rear wall 132 are substantially parallel to one another and substantially perpendicular to the first side wall 136 and the second side wall 140. Likewise, the first side wall 136 and the second side wall 140 are substantially parallel to one another and substantially perpendicular to the front wall 128 and the rear wall 132. This arrangement of the walls forms the hollow rectangular prism shape of the main body 104. However, it will be appreciated that a hollow rectangular prism shape is also accomplished by embodiments in which the walls are not quite planar and/or in which the walls are arranged not quite mutually orthogonally. For the purposes of this disclosure, the term "hollow rectangular prism" means a shape that has six separate, distinct, rectangularly shaped faces, each defining a plane. The planes intersect at edges that may or may not be beveled, angled, or truncated. Additionally, the faces may be substantially solid or substantially void.

As described herein, the terms "front," "rear," "side(s)," and "end(s)" refer to the orientation of the corpectomy cage 100, and portions thereof, shown in FIG. 1. When the corpectomy cage 100 is inserted into the patient's body, the corpectomy cage 100 is oriented such that the front is facing directly toward the surgical opening, and once the corpectomy cage 100 has been implanted, the corpectomy cage 100 is oriented such that the rear is facing directly out of the surgical opening. Accordingly, the sides and ends of the corpectomy cage 100 are received within the surgical opening and face directly toward tissue within the surgical opening. The ends face toward the remaining vertebral bodies and/or discs to maintain the desired spacing between the remaining vertebral bodies and/or discs.

The first end 116 and the second end 120 of the main body 104 are made up of the front wall 128, the rear wall 132, the first side wall 136, and the second side wall 140. The first end 116 includes a first end surface 148 that is defined by end surfaces of the front wall 128, rear wall 132, first side wall 136, and second side wall 140. Likewise, the second end 120 includes a second end surface 152 that is defined by opposite end surfaces of the front wall 128, rear wall 132, first side wall 136, and second side wall 140. The first end 116 and the second end 120 of the main body 104 are open from the longitudinal opening 144 to the exterior of the main body 104. In other words, the longitudinal opening 144 extends through the first end surface 148 and the second end surface 152. Accordingly, the longitudinal axis 124 of the corpectomy cage 100 is oriented so as to extend through the first end 116 and the second end 120.

Each of the front wall 128 and the rear wall 132 is defined by an inwardly facing surface 156 and an outwardly facing surface 160. The inwardly facing surfaces 156 are those facing toward the longitudinal opening 144, and the outwardly facing surfaces 160 are those on the opposite sides of the front and rear walls 128, 132 that face away from the longitudinal opening 144. In the view shown in FIG. 1, only the inwardly facing surface 156 of the rear wall 132 is visible, and only the outwardly facing surface 160 of the front wall 128 is visible.

Figure 2D:
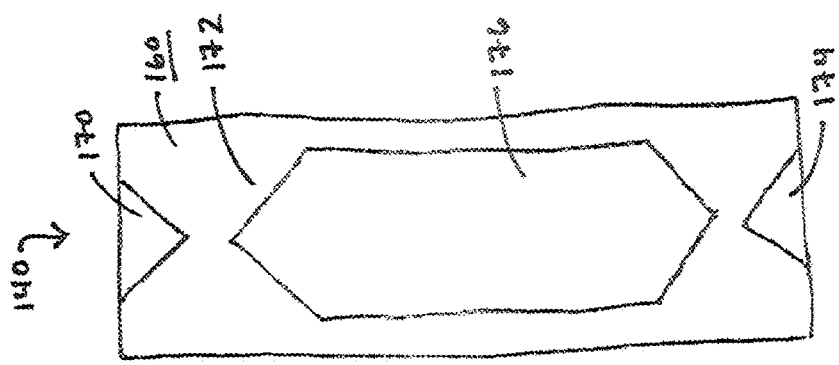
FIG. 2D depicts a schematic view of a second side of the main body of the corpectomy cage shown in FIG. 1.
Figure 2C:
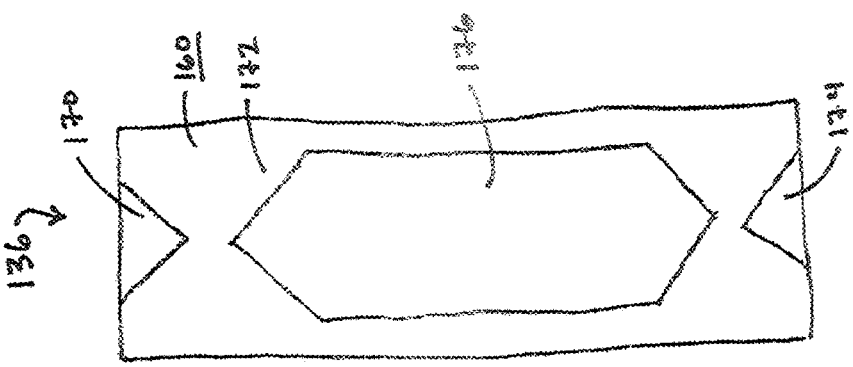
FIG. 2C depicts a schematic view of a first side of the main body of the corpectomy cage shown in FIG. 1.
Figure 2B:
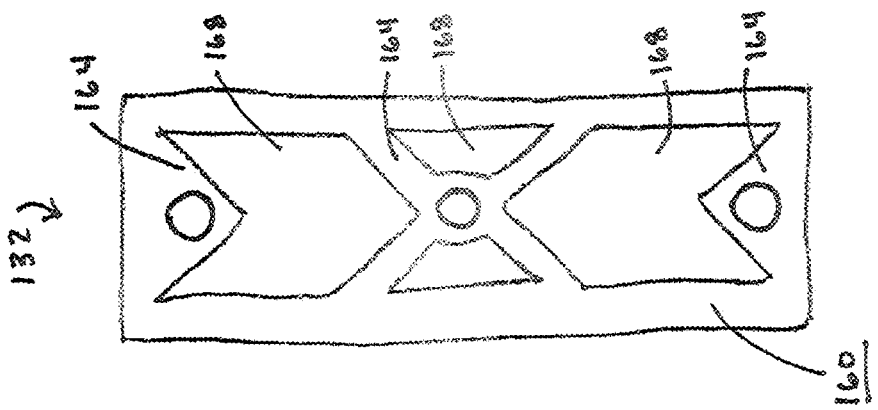
FIG. 2B depicts a schematic view of a rear of the main body of the corpectomy cage shown in FIG. 1.
Figure 2A:
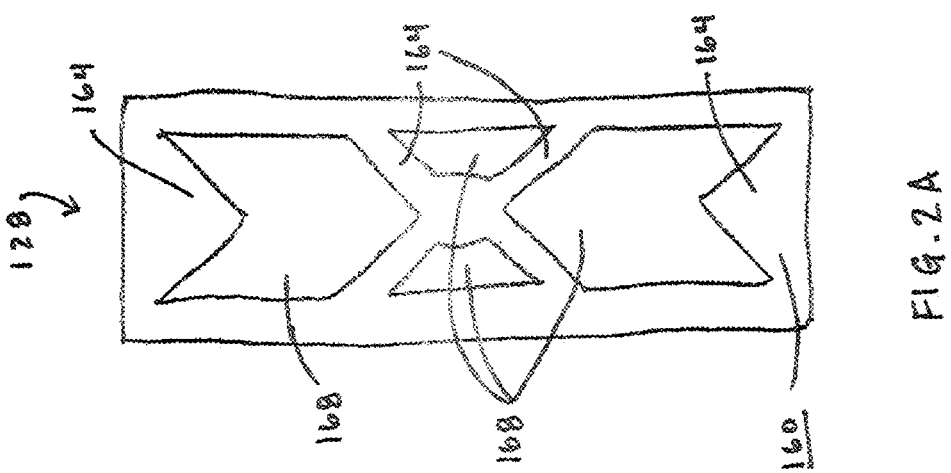
FIG. 2A depicts a schematic view of the front of the main body of the corpectomy cage shown in FIG. 1.

As shown in FIGS. 2A and 2B, each of the front wall 128 and the rear wall 132 includes supports 164 that extend between the first side wall 136 and the second side wall 140. The supports 164 are separated by voids 168 formed in the front and rear walls 128, 132. Accordingly, each of the front and rear walls 128, 132 is made up of the supports 164 and voids 168 formed in the space between a plane that includes the respective inwardly facing surface 156 and a plane that includes the respective outwardly facing surface 160. The voids 168 provide access to the longitudinal opening 144 and the interior of the main body 104 to enable insertion of bone graft into the main body 104 and integration of the bone graft with surrounding native tissue once the corpectomy cage 100 has been implanted. The supports 164 provide structural strength and stability to the front and rear walls 128, 132.

Similarly, as shown in FIG. 1, each of the first side wall 136 and the second side wall 140 is defined by an inwardly facing surface 156 and an outwardly facing surface 160. The inwardly facing surfaces 156 are those facing toward the longitudinal opening 144, and the outwardly facing surfaces 160 are those on the opposite sides of the first and second side walls 136, 140 that face away from the longitudinal opening 144. In the view shown in FIG. 1, only the inwardly facing surface 156 of the second side wall 140 is visible, and only the outwardly facing surface 160 of the first side wall 136 is visible.

As shown in FIGS. 2C and 2D, each of the first and second side walls 136, 140 also includes side supports 172 that extend between the front wall 128 and the rear wall 132. The side supports 172 are separated by side voids 176 formed in the first and second side walls 136, 140. Accordingly, each of the first and second side walls 136, 140 is made up of the side supports 172 and side voids 176 formed in the space between a plane that includes the respective inwardly facing surface 156 and a plane that includes the respective outwardly facing surface 160. Like the voids 168, the side voids 176 provide access to the longitudinal opening 144 and the interior of the main body 104 to enable insertion of bone graft into the main body 104 and integration of the bone graft with surrounding native tissue once the corpectomy cage 100 has been implanted. Like the supports 164, the side supports 172 provide structural strength and stability to the first and second side walls 136, 140.

Each of the first and second side walls 136, 140 further includes a first notch 170 formed in the outwardly facing surface 160 at the first end 116 of the main body 104 and a second notch 174 formed in the outwardly facing surface 160 at the second end 120 of the main body 104. More specifically, as shown in FIG. 1, each of the first notches 170 is a cut-out formed in the side wall 136, 140 that is open to, or extends through, the first end surface 148 and the outwardly facing surface 160, but is not open to, and does not extend through, the inwardly facing surface 156. As explained in further detail below, the first notches 170 are configured to facilitate gripping the first end cap 108 when the first end cap 108 is coupled to the main body 104 to separate or remove the first end cap 108 from the main body 104 by applying force in the direction opposite to the direction indicated by the arrows A. Similarly, each of the second end notches 174 is a cut-out formed in the side wall 136, 140 that is open to, or extends through, the second end surface 152 and the outwardly facing surface 160, but is not open to, and does not extend through, the inwardly facing surface 156. Like the first notches 170, the second notches 174 are configured to facilitate gripping the second end cap 112 when the second end cap 112 is coupled to the main body 104 to separate or remove the second end cap 112 from the main body 104 by applying force in the direction opposite to the direction indicated by the arrows B.

As shown in FIG. 3, the main body 104 is substantially symmetrically formed over a transverse plane TP that passes through the middle of the main body 104 orthogonally to the longitudinal axis 124. Accordingly, the first end 116 and the second end 120 of the main body 104 are substantially similar to one another. More specifically, the first end 116 and the second end 120 are mirror images of one another when reflected over the transverse plane TP. Accordingly, descriptions herein of the first end 116 also apply symmetrically to the second end 120. Additionally, the main body 104 is substantially symmetrically formed over a medial plane MP that passes through the middle of the front and rear walls 128, 132 parallel to the longitudinal axis 124 and orthogonally to the transverse plane TP. Accordingly, the first and second side walls 136, 140 of the main body 104 are mirror images of one another when reflected over the medial plane MP. Additionally, the two halves of the front wall 128 are mirror images of one another and the two halves of the rear wall 132 are mirror images of one another when reflected over the medial plane MP.

Forming the main body 104 symmetrically in this manner enables the main body 104 to be oriented such that the first end 116 is coupled to the first end cap 108 or the second end cap 112 and such that the second end 120 is coupled to the first end cap 108 or the second end cap 112. This reversible arrangement facilitates ease of use of the main body 104 in the corpectomy cage 100. Additionally, the symmetries of the main body 104 facilitate ease of production of the main body 104 and a symmetrically even distribution of forces and stresses on the main body 104 in use.

Figure 4:
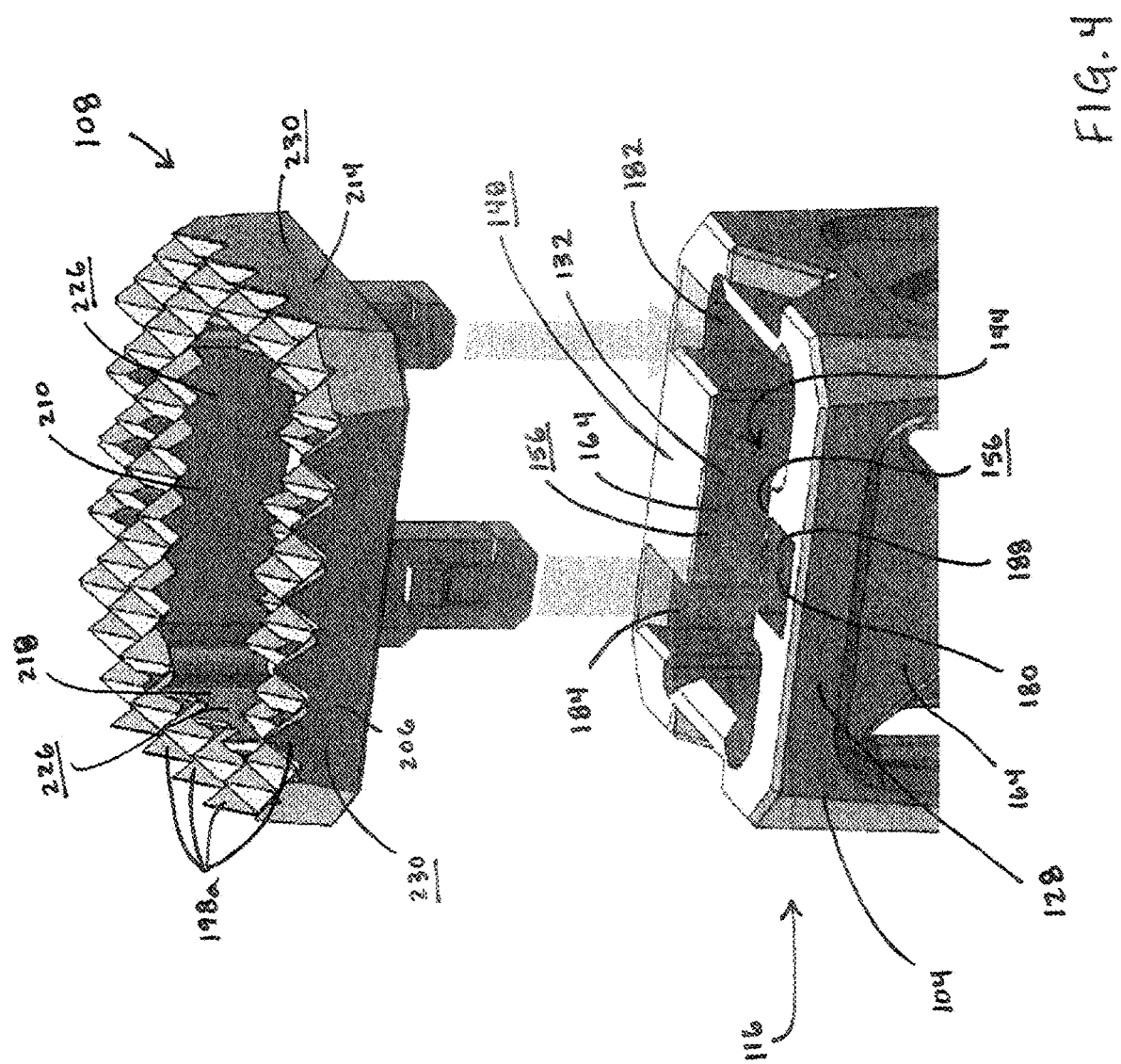
FIG. 4 depicts a partial exploded perspective view of the corpectomy cage as shown in FIG. 1.

As shown in FIG. 4, the first end 116 of the main body 104 includes a plurality of receivers 180, 182, 184 formed therein. As described in further detail below, each of the receivers 180, 182, 184 is configured to receive a corresponding leg of the first end cap 108 to removably engage the first end cap 108 with the first end 116 of the main body 104. Accordingly, each of the receivers 180, 182, 184 extends through the first end surface 148, forming a cavity in the first end 116 of the main body.

A front receiver 180 of the plurality of receivers is a blind hole formed in the front wall 128. More specifically, the front receiver 180 is open through the first end surface 148, but is not open through the inwardly facing surface 156 of the front wall 128 to the longitudinal opening 144. Additionally, because the front receiver 180 is a blind hole, rather than a through hole, it is formed to a specific depth and does not break through any surface opposite the first end surface 148. Accordingly, to accommodate the depth and girth of the blind hole, the front receiver 180 is formed in a support 164 of the front wall 128 and is separated from the longitudinal opening 144 by a separating wall 188 that is formed integrally with the front wall 128 and is coextensive with the inwardly facing surface 156 of the front wall 128. As used herein, the term "coextensive" refers to two elements, such as surfaces, that extend in one direction to a common plane. In the case of the separating wall 188, the separating wall 188 and the inwardly facing surface 156 of the front wall 128 extend in the direction toward the longitudinal opening 144 to a common plane. Forming the front receiver 180 within the support 164 of the front wall 128 in this manner ensures a secure and stable connection between the first end cap 108 and the first end 116 of the main body 104.

Rear receivers 182, 184 of the plurality of receivers are open or interrupted holes formed in the rear wall 132. More specifically, each of the rear receivers 182, 184 extends through the first end surface 148, and also extends through the inwardly facing surface 156 of the rear wall 132 to the longitudinal opening 144. Moreover, the rear receivers 182, 184 are through holes, and therefore also extend through a surface opposite the first end surface 148.

In particular, the rear receivers 182, 184 are formed in a support 164 of the rear wall 132 and are open to the longitudinal opening 144. Additionally, the rear receivers 182, 184 extend through the support 164 to the adjacent void 168 (not visible in FIG. 3). Forming the rear receivers 182, 184 as interrupted holes makes reception of the corresponding legs of the first end cap 108 within the rear receivers 182, 184 easier relative to that of the front receiver 180. Forming the rear receivers 182, 184 within the support 164 of the rear wall 132 also ensures a secure and stable connection between the first end cap 108 and the first end 116 of the main body 104.

The rear receivers 182, 184 are formed in the rear wall 132 at positions that are offset relative to the position of the front receiver 180 in the front wall 128 when viewing the main body 104 in a direction along the medial plane MP. In particular, the front receiver 180 is formed on the medial plane MP, while the rear receivers 182, 184 are each spaced apart from the medial plane MP. Offsetting the receivers 182, 180, 184 provides additional strength and stability to the engagement between the first end cap 108 and the first end 116 of the main body 104.

Figure 5:
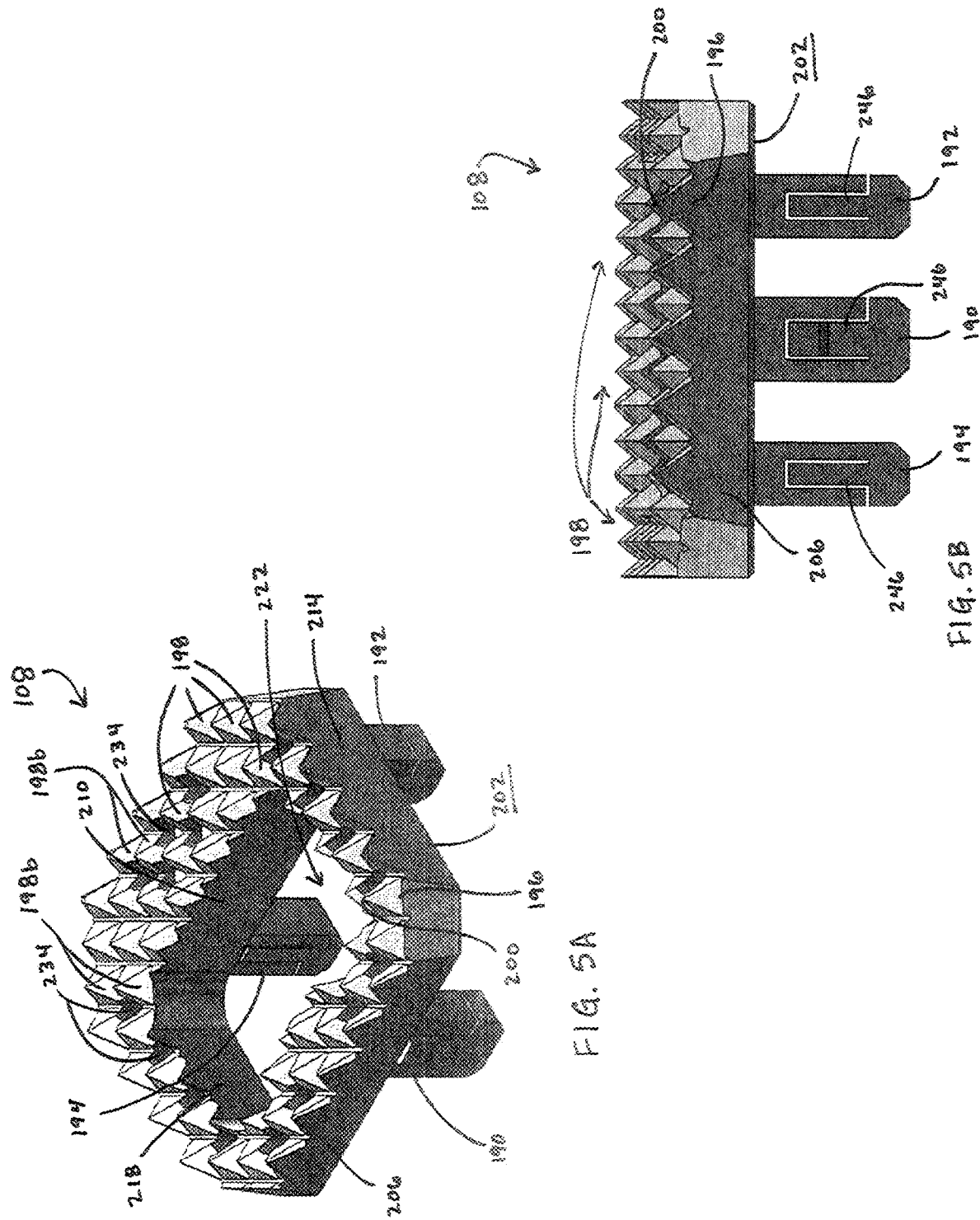
FIG. 5A depicts a perspective view of one of the two end caps of the corpectomy cage shown in FIG. 1.
FIG. 5B depicts a front elevational view of the end cap shown in FIG. 5A.

Turning now to FIGS. 5A and 5B, the first end cap 108 is shown in greater detail. The first end cap 108 and the second end cap 112 are substantially similar to one another. Accordingly, while only the first end cap 108 is described below, the description of the first end cap 108 also applies to the second end cap 112.

The first end cap 108 includes a plurality of legs 190, 192, 194 arranged opposite a plurality of teeth 198. As used herein, the term "opposite" means in the opposing direction along a common axis. Accordingly, the legs 190, 192, 194 the first end cap 108 in a first direction, along a first axis, and the plurality of teeth 198 extend from the first end cap 108 in the opposite direction along the same first axis.

The legs 190, 192, 194 are integrally formed with the first end cap 108 and extend from a base surface 202 of the end cap 108 in a direction that is substantially perpendicular to the base surface 202. Each of the legs 190, 192, 194 is arranged and configured to be received in a corresponding receiver 180, 182, 184 to removably engage the first end cap 108 with the first end 116 of the main body 104 as shown in FIG. 1. Accordingly, the legs 190, 192, 194 include a front leg 190, arranged and configured to be received in the front receiver 180, and rear legs 192, 194 arranged and configured to be received in the rear receivers 182, 184.

The plurality of teeth 198 are integrally formed with the first end cap 108 and extend from the opposite side of the end cap 108 as the legs 190, 192, 194. In particular, each of the teeth 198 has a tooth base 196, which is arranged nearest to the base surface 202, and a tooth tip 200, which is arranged farthest from the base surface 202. The teeth 198 are configured to engage the ends of the corpectomy cage 100 with the remaining vertebral bodies or discs to anchor the corpectomy cage 100 into the tissue at the surgical site.

In the embodiment shown, the plurality of teeth 198 cover each of the cap walls 206, 210, 214, 218, opposite the base surface 202, from the cap inwardly facing surfaces 226 to the cap outwardly facing surfaces 230. In other words, the plurality of teeth 198 cover the entirety of the first end cap 108 opposite the base surface 202. In alternative embodiments, the plurality of teeth 198 can be arranged to cover less than the entirety of the first end cap 108. However, covering the entirety of the first end cap 108 is preferable, because it maximizes the number of points of engagement between the plurality of teeth 198 and the surrounding tissue when the corpectomy cage 100 is implanted.

The first end cap 108 also includes a front cap wall 206, a rear cap wall 210, first side cap wall 214, and a second side cap wall 218. Each of the cap walls 206, 210, 214, 218 extends from the base surface 202 to the plurality of teeth 198 in a direction that is substantially parallel to the directions in which the legs 190, 192, 194 extend. Like the walls 128, 132, 136, 140 that make up the main body 104, the cap walls 206, 210, 214, 218 that make up the first end cap 108 delimit a cap longitudinal opening 222.

Figure 6:
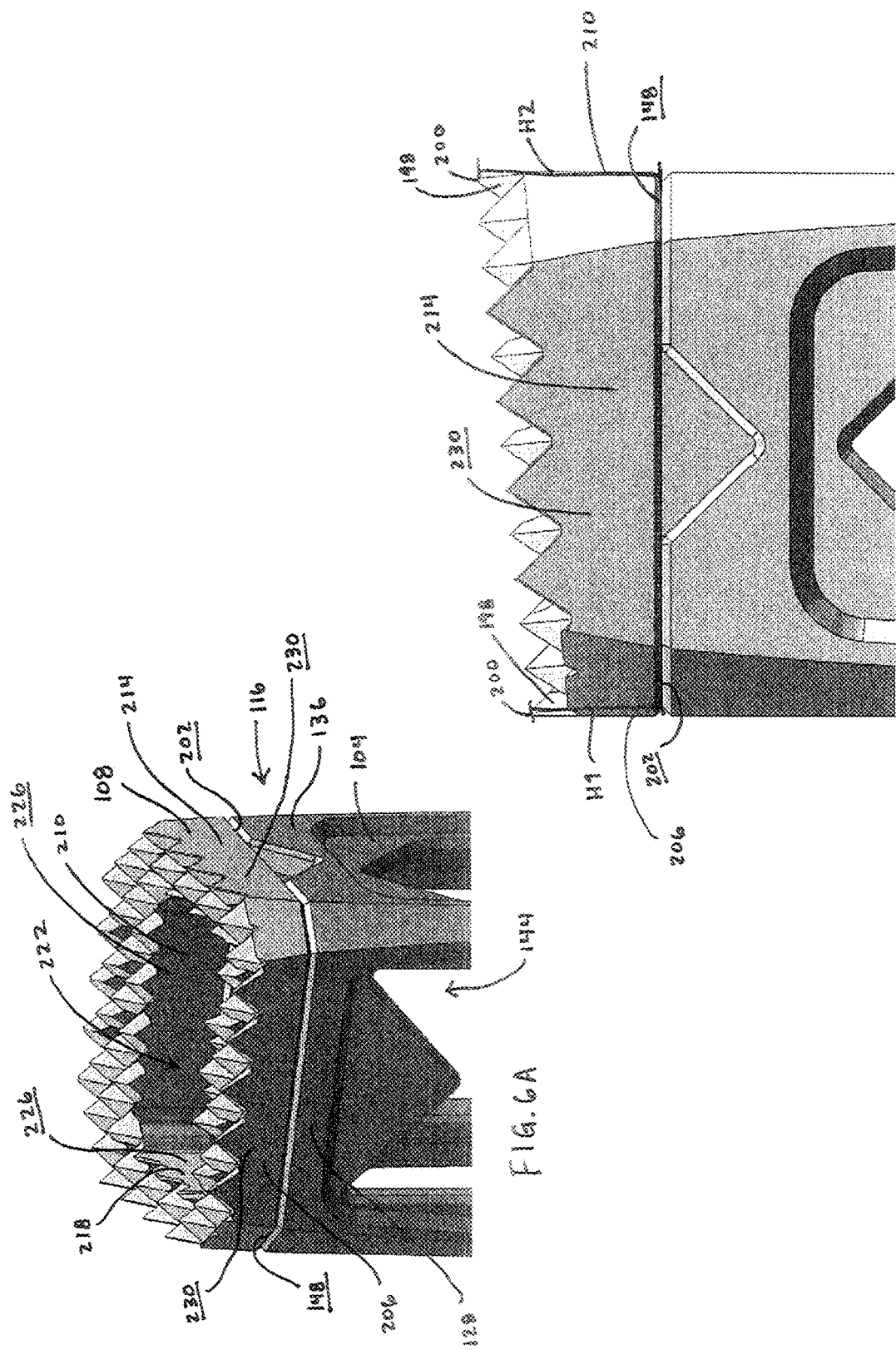
FIG. 6A depicts a partial perspective view of the end cap shown in FIGS. 4A and 4B engaged with the main body of the corpectomy cage shown in FIG. 1.
FIG. 6B depicts a partial side elevational view of the end cap shown in FIGS. 4A and 4B engaged with the main body of the corpectomy cage as shown in FIG. 6A.

As shown in FIGS. 6A and 6B, when the first end cap 108 is engaged with the first end 116 of the main body 104, the base surface 202 is in direct contact with and rests on the first end surface 148, each of the cap walls 206, 210, 214, 218 is aligned with the corresponding wall 128, 132, 136, 140 of the main body 104, and the cap longitudinal opening 222 is aligned with the longitudinal opening 144.

More specifically, like the walls 128, 132, 136, 140 of the main body 104, each of the walls 206, 210, 214, 218 of the first end cap 108 includes a cap inwardly facing surface 226, facing toward the cap longitudinal opening 222 and toward the other cap inwardly facing surfaces 226, and a cap outwardly facing surface 230, facing in the opposite direction, away from the cap longitudinal opening 222. When the first end cap 108 is engaged with the first end 116 of the main body 104, the cap inwardly facing surfaces 226 are aligned with and coextensive with the inwardly facing surfaces 156 of the main body 104 and the cap outwardly facing surfaces 230 are aligned with and coextensive with the outwardly facing surfaces 160 of the main body 104. In particular, the cap inwardly facing surface 226 of each of the cap walls 206, 210, 214, 218 extends in the direction toward the longitudinal axis 124 to the same plane as the inwardly facing surface 156 of the corresponding wall 128, 132, 136, 140 of the main body 104, and the cap outwardly facing surface 230 of each of the cap walls 206, 210, 214, 218 extends in the direction away from the longitudinal axis 124 to the same plane as the outwardly facing surface 160 of the corresponding wall 128, 132, 136, 140 of the main body 104.

As shown in FIG. 6B, a height of the first end cap 108 is different at the front cap wall 206 than at the rear cap wall 210. In particular, the cap outwardly facing surface 230 of the front cap wall 206 extends a first height H1 from the base surface 202 to the tooth tips 200 of the teeth 198 that are coextensive with the cap outwardly facing surface 230 of the front cap wall 206, and the cap outwardly facing surface 230 of the rear cap wall 210 extends a second height H2 from the base surface 202 to the tips 242 of the teeth 198 that are coextensive with the cap outwardly facing surface 230 of the rear cap wall 210. The first height H1 is less than the second height H2. This arrangement of the heights of the first end cap 108 facilitates engagement of the corpectomy cage 100 within the corpectomy site. In particular, the difference between the first height H1 and the second height H2 over the distance between the outwardly facing surfaces 230 of the front and rear cap walls 206, 210 creates a lordotic angle of the first end cap 108. The first height H1 of the first end cap 108 is matched to the height of the surgical opening to maintain the desired spacing between remaining vertebral bodies and/or discs, and the lordotic angle of the first end cap 108 is matched to the angle to maintain the desired angular relationship between the vertebral bodies and/or discs when the corpectomy cage 100 is implanted in the patient's body.

The height of each of the teeth 198, from the tooth base 196 to the tooth tip 200, of the first end cap 108 is the same. Additionally, the height of the front cap wall 206, from the base surface 202 to the tooth bases 196 of the teeth 198 formed on the front cap wall 206, is constant, and the height of the rear cap wall 210, from the base surface 202 to the tooth bases 196 of the teeth 198 formed on the rear cap wall 206, is constant. Accordingly, the difference between the first height H1 and the second height H2, and the resulting lordotic angle, are created by a change in size of the first and second side cap walls 214, 218 as they extend from the front cap wall 206 to the rear cap wall 210.

The removable engagement between each of the first and second end caps 108, 112 and the main body 104 enables end caps having different heights and lordotic angles to be attached and removed interchangeably on the respective first and second ends 116, 120 of the main body 104 to form a corpectomy cage 100 having a geometry matching the desired spacing and angular relationship as closely as possible. The removability and interchangeability of the first and second end caps 108, 112 enables a surgeon to choose a desired end cap geometry during surgery, once the specific dimensions of the surgical opening are known. Additionally, the surgeon is able to use trial and error by selecting an end cap geometry and testing it within the surgical opening and then being able to remove it and test another end cap before committing to the end cap that will be used with the corpectomy cage in the patient's body.

Figure 7:
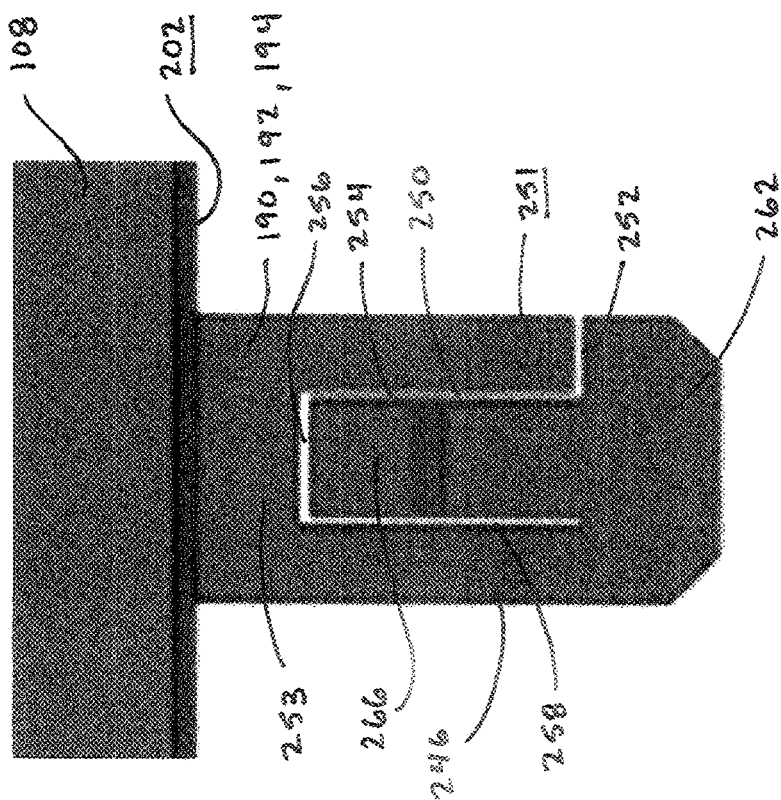
FIG. 7 depicts a partial front elevational view of the end cap shown in FIG. 5B including a leg of the end cap.

To facilitate removable, but also ensure secure attachment between the end cap 108 and the main body 104, each of the legs 190, 192, 194 includes a spring tab 246. Shown in more detail in FIG. 7, each spring tab 246 is formed by a cut 250 in the leg 190, 192, 194. Each cut 250 includes a first horizontal region 252, which extends from an exterior surface 251 into the body 253 of the leg 190, 192, 194 in a direction that is generally parallel to the base surface 202. Each cut 250 also includes a first vertical region 254, which extends from the first horizontal region 252 upwardly through the body 253 of the leg 190, 192, 194 in a direction toward the base surface 202. Each cut 250 further includes a second horizontal region 256, which extends from the first vertical region 254 laterally through the body 253 of the leg 190, 192, 194 in a direction away from the exterior surface 251. Each cut 250 also includes a second vertical region 258, which extends from the second horizontal region 256 downwardly through the body 253 of the leg 190, 192, 194 in a direction away from the base surface 202. The cut 250 thus creates flexibility in each leg 190, 192, 194 by weakening the body 253. More specifically, the cut 250 partially separates a spring portion 262 of each leg 190, 192, 194 from the remainder of the body 253 of the leg 190, 192, 194. The spring portion 262 is flexible relative to the remainder of the body 253 of the leg 190, 192, 194. However, the spring portion 262 is biased toward the resting position wherein the spring portion 262 is aligned with the remainder of the body 253 of the leg 190, 192, 194. This bias generates a spring force in the spring tab 246.

Each spring tab 246 further includes a latch 266, which projects from the spring portion 262 and is configured to engage with a matingly shaped latch receiver 270 formed in the corresponding receiver in the manner shown in FIGS. 8A and 8B. The latch 266 projects from the spring portion 262 in a direction away from the cap longitudinal opening 222 such that the latch 266 stands proud relative to the rest of the respective leg 190, 192, 194. To receive the latch 266 of the front leg 190, the front receiver 180 includes a latch receiver 270 formed within the cavity formed by the blind hole, such that it is open facing toward the separating wall 188 (shown in FIG. 4). To receive the latches 266 of the respective rear leg 192, 194, each of the rear receivers 182, 184 includes a latch receiver 270 formed within the channel formed by the through hole, such that it is open facing toward the longitudinal opening 144.

When the end cap 108 is coupled to the first end 116 of the main body 104 by applying force in the direction indicated by the arrows A (shown in FIG. 1), the legs 190, 192, 194 are received in the corresponding receivers 180, 182, 184 and the latches 266 are forced inwardly, toward the cap longitudinal opening 222, by the receivers 180, 182, 184. The inward movement of each of the latches 266 is accommodated by the corresponding spring portion 262, which allows the corresponding spring tab 246 to flex inwardly as the latches 266 are forced downwardly until the latches 266 pass into the corresponding latch receivers 270. When the latches 266 pass into the corresponding latch receivers 270, the spring force generated by the spring tabs 246 forces the spring portions 262 outwardly, away from the cap longitudinal opening 222 and secures the latches 266 within the latch receivers 270 to securely attach the first end cap 108 to the main body 104.

To remove the first end cap 108 from the main body 104, the spring force generated by the spring tabs 246 must be overcome to release the latches 266 from the latch receivers 270. To overcome the spring force, the first end cap 108 is gripped at the base surface 202 on the first and second cap side walls 214, 218 via the first notches 170 and pulled in the direction away from the main body 104. When the pulling force is sufficient to overcome the spring force of the spring tabs 246, the latches 266 slip inwardly out of the latch receivers 270, and the legs 190, 192, 194 are removable from the receivers 180, 182, 184.

This attachment and removal mechanism provides a secure attachment and also enables interchangeability. Accordingly, the corpectomy cage 100 achieves the superior structural integrity of a fixed height cage by way of the main body 104, and also achieves adjustability of height and/or lordotic angle by way of the interchangeable first and second end caps 108, 112. For example, as shown in FIG. 9, the corpectomy cage 100 can be assembled from a kit 300, which includes at least one main body 104, and a plurality of first and second end caps 108a, 108b, 108c, 112a, 112b, 112c configured to be removably engaged with the main body 104. Each of the first end caps 108a, 108b, 108c can have a different height H1 (shown in FIG. 6A) and/or a different lordotic angle to provide the surgeon with multiple choices to optimize the fit of the corpectomy cage 100 in the surgical site and the post-operative spacing and angle maintained by the corpectomy cage 100. Similarly, each of the second end caps 112a, 112b, 112c can have a different height H1 and/or a different lordotic angle. Additionally, because the main body 104 is symmetrical, the first and second end caps 108, 112 can be used interchangeably on the first and second ends of the main body 104, providing the surgeon with even more options.

In the embodiment shown in FIG. 2B, the rear wall 132 of the main body 104 includes threaded holes 274 extending through the supports 164 in a direction toward the longitudinal axis 124. The threaded holes 274 are configured to threadably engage an insertion tool (not shown) used by the surgeon to guide and place the corpectomy cage 100 in the surgical site and to facilitate removal of the corpectomy cage 100 from the surgical site for adjustments or to exchange the first and/or second end cap 108, 112 prior to completing implantation of the corpectomy cage 100. Accordingly, the threaded holes 274 enable guidance, placement, and removal of the corpectomy cage 100 from the surgical site without extraneous contact or disruption of the surgical site and surrounding tissue. In alternative embodiments, alternative features may be used to facilitate guidance, placement, and removal of the corpectomy cage 100 from the surgical site without extraneous contact with the surgical site and surrounding tissue.

In the embodiment shown in FIG. 4, some of the teeth 198a that are arranged at the cap inwardly and outwardly facing surfaces 226, 230 are coextensive with the walls 206, 210, 214, 218. In other words, some of the teeth 198a are truncated at the surfaces 226, 230 and therefore only form partial teeth 198a. This arrangement of the teeth 198 ensures that the entirety of the end cap 108 is covered with teeth 198 and also allows the teeth 198 to be regularly spaced over the entirety of the end cap 108. In alternative embodiments, different arrangements of the plurality of teeth 198 are possible on the first end cap 108 opposite the base surface 202 that do not result in truncated teeth 198a.

In the embodiment shown in FIGS. 5A and 6A, the first end cap 108 further includes a plurality of through holes 234, which extend through each of the cap walls 206, 210, 214, 218 in a direction substantially parallel to that at which the legs 190, 192, 194 extend. The through holes 234 extend through the base surface 202 and extend through the plurality of teeth 198 to further facilitate integration of the corpectomy cage 100 with the bone and tissue at the corpectomy site upon implantation. In particular, the through holes 234 interrupt or truncate the teeth 198b between which they extend. In the embodiment shown, the through holes 234 and the teeth 198 are arranged such that the through holes 234 only interrupt teeth 198b near their bases 196, rather than near their tips 200. This arrangement preserves the tips 200 of the teeth 198b to facilitate engagement of the first end cap 108, and thus the corpectomy cage 100, with the bone and tissue of the remaining vertebral bodies or discs at the corpectomy site upon implantation.

What is claimed is:

1. A corpectomy cage, comprising:
    a main body shaped as a hollow rectangular prism, the main body including a first end having a plurality of first receivers formed therein, the main body further including a second end arranged opposite the first end, the second end having a plurality of second receivers formed therein;
    a first end cap, the first end cap including a plurality of first legs, each first leg configured to be received within a respective first receiver of the plurality of first receivers to removably engage the first end cap with the first end of the main body, the first end cap further including a plurality of first teeth arranged opposite the plurality of first legs; and
    a second end cap, the second end cap including a plurality of second legs, each second leg configured to be received within a respective second receiver of the plurality of second receivers to removably engage the second end cap with the second end of the main body, the second end cap further including a plurality of second teeth arranged opposite the plurality of second legs, wherein;
    the main body includes a front wall, a rear wall arranged opposite the front wall, a first side wall extending from the front wall to the rear wall, and a second side wall extending from the front wall to the rear wall and arranged opposite the first side wall; the front wall, the rear wall, the first side wall, and the second side wall delimit a longitudinal opening of the main body, define a first end surface of the first end of the main body, and define a second end surface of the second end of the main body; and the longitudinal opening extends through the first and second end surfaces, each first receiver extends through the first end surface, and each second receiver extends through the second end surface.

2. The corpectomy cage of claim 1, wherein:
    a front first receiver of the plurality of first receivers is formed in the front wall and is separated from the longitudinal opening by a first separating wall that is formed integrally with the front wall.

3. The corpectomy cage of claim 1, wherein:
    a rear first receiver of the plurality of first receivers is formed in the rear wall and is open to the longitudinal opening.

4. The corpectomy cage of claim 1, wherein:
    each of the first side wall and the second side wall includes an inwardly facing surface, facing toward the longitudinal opening, and an outwardly facing surface, facing away from the longitudinal opening; and
    at least one of the first side wall and the second side wall includes a first notch formed in said outwardly facing surface thereof at the first end of the main body.

5. The corpectomy cage of claim 4, wherein:
    at least one of the first side wall and the second side wall includes a second notch formed in the respectively outwardly facing surface at the second end of the main body.

6. The corpectomy cage of claim 5, wherein:
the at least one first notch extends through the first end surface and the at least one second notch extends through the second end surface.

7. The corpectomy cage of claim 4, wherein:
each of the front wall and the rear wall includes an inwardly facing surface, facing toward the longitudinal opening, and an outwardly facing surface, facing away from the longitudinal opening;
at least one of the first end cap and the second end cap includes a plurality of inwardly facing surfaces configured to be coextensive with the inwardly facing surfaces of the front wall, rear wall, first side wall, and second side wall when the at least one end cap is engaged with the main body.

8. The corpectomy cage of claim 7, wherein:
at least one of the first end cap and the second end cap includes a plurality of outwardly facing surfaces configured to be coextensive with the outwardly facing surfaces of the front wall, rear wall, first side wall, and second side wall when the at least one end cap is engaged with the main body.

9. The corpectomy cage of claim 7, wherein:
the rear wall includes a plurality of supports extending between the first side wall and the second side wall; and
at least one support includes a threaded opening extending through the inwardly facing surface and through the outwardly facing surface of the rear wall.

10. The corpectomy cage of claim 7, wherein:
a rear first receiver of the plurality of first receivers is formed in the rear wall and extends through the inwardly facing surface of the rear wall.

11. The corpectomy cage of claim 1, wherein:
at least one of the first end cap and the second end cap includes a base surface from which said plurality of first legs and said plurality of second legs, respectively, extends; and
when said plurality of first legs and said plurality of second legs, respectively, is received within the respective first receiver and second receiver, the base surface is in direct contact with the first end surface and the second end surface, respectively, of the main body.

12. The corpectomy cage of claim 11, wherein:
the at least one of the first end cap and the second end cap includes at least one hole extending through the base surface and through the corresponding plurality of teeth.

13. The corpectomy cage of claim 1, wherein:
at least one leg of the plurality of first legs and the plurality of second legs includes a spring tab configured to engage with the respective first receiver and second receiver.

14. The corpectomy cage of claim 13, wherein:
the spring tab includes:
a cut in the at least one leg such that a spring portion of the at least one leg is flexible relative to the remainder of the at least one leg; and
a latch projecting from the spring portion and configured to engage with a matingly shaped latch receiver formed in the corresponding receiver.

15. A kit for a corpectomy cage to be implanted into the body of an animal, the kit comprising:
at least one main body shaped as a hollow rectangular prism, the main body including a first end having a plurality of first receivers formed therein, the main body further including a second end arranged opposite the first end, the second end having a plurality of second receivers formed therein;
a plurality of end caps, each end cap including a plurality of legs, each leg configured to be received within one of said plurality of first receivers and said plurality of second receivers to removably engage the end cap with one of the first and second ends of the main body, each end cap further including a plurality of first teeth arranged opposite the plurality of legs, wherein said plurality of end caps each define a different lordotic angle relative to each other, wherein;
the main body includes a front wall, a rear wall arranged opposite the front wall, a first side wall extending from the front wall to the rear wall, and a second side wall extending from the front wall to the rear wall and arranged opposite the first side wall; the front wall, the rear wall, the first side wall, and the second side wall delimit a longitudinal opening of the main body, define a first end surface of the first end of the main body, and define a second end surface of the second end of the main body; and
the longitudinal opening extends through the first and second end surfaces, each first receiver extends through the first end surface, and each second receiver extends through the second end surface.

16. The corpectomy cage of claim 15, wherein:
each of the first side wall and the second side wall includes an inwardly facing surface, facing toward the longitudinal opening, and an outwardly facing surface, facing away from the longitudinal opening; and
at least one of the first side wall and the second side wall includes a first notch formed in said outwardly facing surface thereof at the first end of the main body.

17. The kit of claim 16, wherein:
each end cap includes a plurality of inwardly facing surfaces configured to be coextensive with the inwardly facing surfaces of the front wall, rear wall, first side wall, and second side wall when the end cap is engaged with the main body.

18. The corpectomy cage of claim 15, wherein:
each end cap includes a base surface from which said plurality of legs extends; and
when each of the plurality of legs is received within the respective receiver, the base surface is in direct contact with the respective end surface of the main body.

\* \* \* \* \*